(12) United States Patent
Franchi et al.

(10) Patent No.: US 10,258,561 B2
(45) Date of Patent: Apr. 16, 2019

(54) COSMETIC COMPOSITION CONTAINING A BROWN ALGA EXTRACT, A YEAST EXTRACT AND ASCORBIC ACID

(71) Applicant: LVMH RECHERCHE, Saint Jean de Braye (FR)

(72) Inventors: Jocelyne Franchi, Saint Jean de la Ruelle (FR); Isabelle Renimel, Trainou (FR); Michele Neveu, Orleans (FR); Valerie Gorzelanczyk, Chateauneuf sur Loire (FR); Sabrina Maniguet, Trainou (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 14/770,056

(22) PCT Filed: Feb. 24, 2014

(86) PCT No.: PCT/FR2014/050373
§ 371 (c)(1),
(2) Date: Aug. 24, 2015

(87) PCT Pub. No.: WO2014/131971
PCT Pub. Date: Sep. 4, 2014

(65) Prior Publication Data
US 2016/0008269 A1  Jan. 14, 2016

(30) Foreign Application Priority Data
Feb. 28, 2013 (FR) ..................... 13 51809

(51) Int. Cl.
| *A61K 8/99* | (2017.01) |
| *A61K 8/67* | (2006.01) |
| *A61Q 19/08* | (2006.01) |
| *A61K 8/49* | (2006.01) |
| *A61K 8/9706* | (2017.01) |

(52) U.S. Cl.
CPC .............. *A61K 8/99* (2013.01); *A61K 8/4973* (2013.01); *A61K 8/676* (2013.01); *A61K 8/9706* (2017.08); *A61Q 19/08* (2013.01); *A61K 2800/592* (2013.01)

(58) Field of Classification Search
CPC ..... A61K 8/97; A61K 8/02; A61P 3/02; A61P 17/18; A61P 29/00; A61P 39/04; A61P 17/00; A61Q 17/04; A61Q 19/00; A61Q 19/06
See application file for complete search history.

(56) References Cited

U.S. PATENT DOCUMENTS

| 5,215,759 A | * | 6/1993 | Mausner | A61K 8/11 |
| | | | | 424/195.16 |
| 2002/0192765 A1 | | 12/2002 | Scholz et al. | |
| 2003/0031692 A1 | * | 2/2003 | Jager Lezer | A61K 8/88 |
| | | | | 424/401 |

FOREIGN PATENT DOCUMENTS

| DE | 102007024384 | * | 11/2008 | ............... A61K 8/97 |
| EP | 1514537 | * | 3/2005 | ............... A61K 7/48 |
| EP | 1938789 | | 7/2008 | |
| WO | 2010145008 | | 12/2010 | |
| WO | 2011116216 | | 9/2011 | |
| WO | WO 2011/116216 | * | 9/2011 | ............... A61K 8/97 |
| WO | WO 2012011907 | * | 1/2012 | ............. A61Q 19/02 |
| WO | WO 2012072951 | * | 6/2012 | ............... A61K 8/99 |

OTHER PUBLICATIONS

Mintel: "Dimple Vanisher"; Database GNPD [Online], XP055004233, Sep. 2009, pp. 1-6.
Mintel: "SkinPerfecting Serum"; Database GNPD, XP002715412, Feb. 2007, pp. 1-2.
Dumas et al.: "In Vitro biosynthesis of type I and III collagens by human dermal fibroblasts from donors of increasing age"; Mechanisms of Ageing and Development, 1994, pp. 179-187.
Basf: "Manufacturing Process Seanergilium BG ref. ALVM002A"; Jul. 2008.
Arch: "Manufacturing Procedure for Water & *Saccharomyces lysate* Extract".

* cited by examiner

*Primary Examiner* — Jana A Hines
(74) *Attorney, Agent, or Firm* — Hamre, Schumann, Mueller & Larson, P.C.

(57) ABSTRACT

The invention relates to a cosmetic composition comprising at least one cosmetically acceptable excipient and from 0.01 to 1% by weight, preferably from 0.05 to 0.6%, and more preferably from 0.1 to 0.3% by weight of the combination of an extract of the brown alga *Laminaria digitata*, of a *Saccharomyces* hydrolysate and of ascorbic acid or one of its esters, the percentage being expressed by dry weight.

The combination of active agents of the invention for which a synergistic effect with regard to the synthesis of the procollagen I has been shown also produces an advantageous effect with regard to other markers of aging.

10 Claims, No Drawings

COSMETIC COMPOSITION CONTAINING A BROWN ALGA EXTRACT, A YEAST EXTRACT AND ASCORBIC ACID

The subject matter of the invention is a cosmetic care composition containing a normal combination of three cosmetic active agents selected for the synergistic effect which they provide with regard to the synthesis of type I collagen and its precursor, procollagen I, in senescent dermal fibroblasts in culture. The combination of these three active agents is also effective with regard to four other markers of skin aging after topical application to skin explants under survival conditions.

The cosmetic composition of the invention is particularly of use as care product for the skin for combating the decrease in the firmness of the skin, in particular as restructuring and toning anti-aging cosmetic agent for aged skin.

PRIOR ART

Fibroblasts are the main cells of the dermis and are specialized in the synthesis of the fibers of the extracellular matrix constituting the dermis, in particular collagen fibers.

Collagen is thus the main supporting protein of the skin arranged in a triple helix, on which it confers resistance to tensions and tractions.

During aging, the lack of collagen in the dermis is one of the main causes of the formation of wrinkles. With age, this supporting tissue of the skin becomes weaker: the collagen fibers degrade, their natural renewal is slower, the dermis loses its density and its mechanical properties, it becomes thinner, wrinkles and fine lines appear, and the contours of the face sag.

A study has shown a significant decrease in the ability to synthesize type I collagen by the fibroblasts of elderly donors (Dumas M. et al., *Mech. Aging Dev.;* 1994, 73, 179-82).

In this context, it appears essential to restart the synthesis of collagen in vivo in order to effectively combat skin aging, in particular in the dermis. This can in particular be achieved by stimulating the synthesis of the precursor of collagen I, procollagen I.

The inventors have found a combination of three ingredients which act synergistically to restart the synthesis of type I collagen and of its precursor, procollagen I, in senescent dermal fibroblasts at a very high level.

These active ingredients are known as anti-aging agents, in particular for their activity with regard to the synthesis of collagen; nevertheless, it has never been shown to date that such a combination can produce a synergy particularly noteworthy with regard to the synthesis of type I collagen or of its precursor. The combination of active agents individually exhibiting an anti-aging activity does not necessarily exhibit an anti-aging activity, as is demonstrated by the inventors in examples which follow. In particular, the combination of two active agents known as anti-aging can have a lower activity than the sum of the activities of the two active agents taken separately, and a combination of these two same active agents with a third can be endowed with an exceptional anti-aging activity. The combination of active agents used in the context of the invention is, in addition, also capable of stimulating other markers involved in skin aging, such as GAGs and elastin but also integral beta-1.

Glycosaminoglycans (or GAGs) are complex polysaccharides, generally sulfated, found in abundance at the surface of cells and in the extracellular matrix. The polarity and the hydrophilic properties of GAGs cause them to implicitly participate in certain biological functions.

Neutral GAGs, observed in the basal membranes, such as the dermo-epidermal junction, around vessels and skin annexes, are an important reservoir of growth factors by virtue of their function of fixing cations and of ion and macromolecular filter, making it possible to concentrate them in the area surrounding the cell in order to play their metabolic role.

Acidic GAGs (essentially hyaluronic acid, a non-sulfated GAG), which are strongly involved in the hydration process by virtue of their ability to retain water, confer on the skin its properties of elasticity and maintenance of the extracellular medium. They are located mainly in the papillary dermis and in the interkeratinocyte spaces of the epidermal basal layers. The dermis includes half of the hyaluronic acid of the body.

These two types of GAGs constitute the bulk of the extracellular matrix. In vivo, GAGs are involved in the elasticity and the hydration of the skin. The metabolism and the renewal of the GAGs, and also the composition of the GAG chains, depend closely on the physiological state of the tissue. In the aging process, the synthesis of GAGs is modified; this is the case for hyaluronic acid, which represents approximately 50% of skin GAGs, the synthesis of which is reduced.

It is thus useful to be able to stimulate the synthesis of these GAGs during aging in order to maintain their positive effects on the maintenance of the firmness of the skin.

Elastin confers, on the elastic fibers of the dermis, the elasticity and the resilience and allows the skin to resume its original position when it is pinched or stretched. Elastin is synthesized and secreted in the extracellular space by the fibroblast and represents up to 90% of the elastic fibers. Elastin and collagen are the main constituents of the extracellular matrix. The total production of elastin stops around puberty, after which the amount of elastin available will decrease with time.

Exposure to ultraviolet radiation increases the degradation of the elastin. The most well-known change of photoaging is the presence in the reticular dermis of solar elastosis, which results from the accumulation of material consisting of abnormal elastin and of other proteins of the extracellular matrix, such as fibronectin or fibrillin. The network of elastic fibers then shows fibers which are often fragmented, thickened and nonfunctional.

Elastin plays a crucial role in the maintenance of elastic skin; it is thus particularly useful to be able to simulate the synthesis thereof in order to prevent or slow down signs of skin aging.

Integrins are transmembrane proteins, one of the ends of which interacts with the substance located outside the cell, the other end interacting with intracellular constituents. The majority of them bind to the molecules of the extracellular matrix and to acting microfilaments via a certain number of binding proteins which are combined with an intracellular region. Integrins play a very important role in the migration, differentiation and survival of cells.

An action with regard to this mark is thus particularly desired for an anti-aging effectiveness.

DESCRIPTION OF THE INVENTION

The composition of the invention comprises the combination of a brown alga extract, of a yeast extract and of ascorbic acid or one of its esters. It has in particular an effect on the synthesis of type I collagen in aged dermal fibroblasts in culture.

There has been shown, for the combination of these three cosmetic active agents, a synergistic effect on the synthesis of type I collagen and of its precursor, procollagen I: these ingredients have actions which reinforce the capability for the synthesis of type I collagen by aged fibroblasts.

The inventors have found that the composition of the invention has a strong potential for stimulating type I collagen and its precursor, even though all the concentrations of active agents are low, which makes it possible to reduce the amounts introduced into the formulations and the cost price of the cosmetic products.

The combination of cosmetic active agents which is used in the context of the invention also exhibits the advantage of being easily formulated, for example by dissolution in the aqueous phase, which makes it possible to produce a wide range of care and makeup anti-aging cosmetic products having highly varied textures and formulation foams ranging from a cream to a stick.

Thus, a first subject matter of the invention relates to a cosmetic composition comprising a cosmetically acceptable excipient and the combination of an extract of the brown alga *Laminaria digitata*, of a *Saccharomyces cerevisiae* hydrolysate and of ascorbic acid or of one of its esters.

The combination of the three active ingredients represents, in total, preferably from 0.01 to 1% by weight, with respect to the weight of the composition, the percentage being expressed by dry weight of the combination, preferably from 0.05 to 0.6% and more preferably from 0.1 to 0.3% by weight.

The concentration of extract of the brown alga *Laminaria digitata* and the compositions preferably between 0.005 and 0.02%, preferably between 0.007 and 0.015%, and more preferably between 0.009 and 0.011% by weight, with respect to the weight of the composition, the percentage being expressed by dry weight of extract.

In one embodiment, the brown alga extract is obtained by grinding the fresh alga, followed by a maceration in water, by separation, by settling and by filtration, each of these stages being carried out under controlled conditions of stirring, pH and duration. A preservative, such as a glycol, can be added at the end of the reaction.

Such an extract can be dissolved in a polar solvent, such as a glycol, for example butylene glycol, or a mixture of a glycol and water.

The INCI name of the brown alga extract can be *Laminaria digitata* extract (and) Butylene Glycol.

The concentration of the *Saccharomyces* hydrolysate in the composition is preferably between 0.001 and 0.05%, preferably between 0.003 and 0.01% and more preferably between 0.004% and 0.006% by weight, with respect to the weight of the composition, percentages being expressed by dry weight of the hydrolysate.

In one embodiment, the *Saccharomyces* hydrolysate is obtained by enzymatic hydrolysis of a baker's yeast *Saccharomyces cerevisiae*. A hydrolysate within the meaning of the invention is not a simple leaven, because said hydrolysate is targeted at hydrolyzing the yeasts, and not at culturing the yeasts. The biological properties of a hydrolysate are thus not necessarily analogous to those that are leaven of the same microorganism.

The *Saccharomyces* hydrolysate can be obtained by radiation of a suspension of the living yeast with UV light and/or heat, hydrolysis by a proteolytic enzyme and collection of the filtrate.

More specifically, the *Saccharomyces* hydrolysate can be obtained by culturing *Saccharomyces*, in particular *Saccharomyces cerevisiae*. The living yeasts are subsequently subjected, in their culture medium, to radiation by a source of UV light and/or a source of heat. This irradiation places the yeasts in a state of stress and brings about, after a certain exposure time, complex biochemical protection mechanisms. When the protection mechanisms have ended, the yeasts are separated from the culture medium and the hydrolysis by a proteolytic enzyme is carried out. When the hydrolysis reaction has ended, the enzyme is deactivated by heating it, for example at 80° C., for one hour. The cell walls are subsequently removed by filtration. The dry matter content of the extract can be adjusted by dilution in water and can reach, for example, 25% by weight.

A *Saccharomyces cerevisiae* hydrolysate can be obtained by the process comprising the series of following stages:
  suspending the living yeast in an appropriate culture medium;
  irradiating the culture medium with UV light and/or by contributing heat in order to place the cells in a situation of stress;
  withdrawing the nutrient medium and lysing the cells of the yeast with a proteolytic enzyme;
  deactivating the enzyme; and
  filtering, in order to remove the cell walls, and collecting the filtrate.

An example of this process is given in the document US 2002/0192765.

The INCI name of the *Saccharomyces* hydrolysate can be Water (and) *Saccharomyces* lysate extract.

The concentration of ascorbic acid or one of its esters can be between 0.05 and 0.5%, preferably between 0.1 and 0.3%, and more preferably between 0.15 and 0.25% by weight, with respect to the weight of the composition.

An ascorbic acid ester can be ascorbyl-2-glucoside of formula (I):

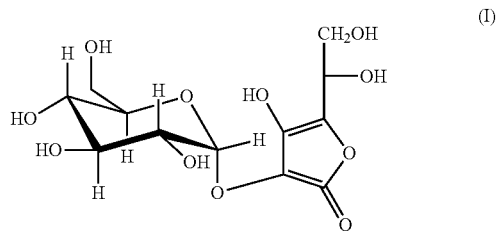

The concentration of ascorbyl-2-glucoside is preferably between 0.05 and 0.5% by weight, with respect to the weight of the composition.

The ratio by weight of the extract of the brown alga *Laminaria digitata* to the *Saccharomyces* hydrolysate is advantageously between 1/1 and 5/1, preferably between 1/1 and 3/1, in particular of the order of 2/1.

The ratio by weight of the ascorbic acid or one of its esters to the *Saccharomyces* hydrolysate is advantageously between 10/1 and 100/1, preferably between 30/1 and 50/1, in particular of the order of 40/1.

According to one aspect of the invention, the composition of the invention is a cosmetic care composition, for example an anti-aging care composition, comprising the combination of the invention as anti-aging active agent and optionally at least one other cosmetic active agent.

Said anti-aging active agent is composed of the combination of an extract of the brown alga *Laminaria digitata*, of a *Saccharomyces* hydrolysate and of ascorbic acid or one of its esters.

In one embodiment, the anti-aging active agent consisting of the combination of an extract of the brown alga *Laminaria digitata*, of a *Saccharomyces* hydrolysate and of ascorbic acid or one of its esters represents between 0.01 and 1% by weight of the weight of the composition, for example of the order of 0.2% by weight.

The cosmetic composition can, in addition, also comprise one or more other cosmetic active agents chosen in particular from those having an anti-aging effect and/or an activity in combating free radicals and/or a depigmenting or lightening effect on the skin and/or a slimming effect and/or a moisturizing effect and/or a calming, soothing or relaxing effect and/or an effect in stimulating skin microcirculation and/or a seboregulating effect and/or a cleaning or purifying effect on the skin.

The composition is preferably devoid of an anti-aging active agent which stimulates the synthesis of collagen other than that described above consisting of the combination and extract of the brown alga *Laminaria digitata*, of a *Saccharomyces* hydrolysate and of ascorbic acid or one of its esters.

The action of the anti-aging active agent of the invention can advantageously be supplemented by the action of other anti-aging agents which act on another target of aging.

In particular, the cosmetic composition can comprise one or more other cosmetic active agents chosen in particular from:
  agents which stimulate the firmness of the skin, such as peptides which stimulate the synthesis of types of collagen other than that of type I, in particular type III or VII collagen, a *Centella asiatica* extract, madecassic acid, asiatic acid, madecassoside, an oats extract, a *Bertholletia excelsa* extract, a protein hydrolysate, soy peptides, a *Potentilla erecta* extract, a *Siegesbeckia orientalis* extract, or ginsenosides or notoginsenosides;
  elastase inhibitors, such as *Aspergillus fumigatus*, *Momordica charantia* or *Cucurbita maxima* extracts;
  agents which stimulate the synthesis of dermatopontin, such as an amber extract;
  agents which close the pores, such as extracts of astringent plants, for example a *Hamamelis* sp. extract;
  physical or chemical screening agents which protect from UV-A and UV-B radiation, such as benzophenone, 4-butyl methoxydibenzoylmethane, octocrylene, ethylhexyl methoxycinnamate, ethylhexyl salicylate, phenylbenzimidazole sulfonic acid or homosalate, alone or in combination with titanium oxides;
  agents intended to combat disorders of pigmentation, in particular those related to skin aging, such as kojic acid, blackberry or licorice root extracts, arbutin, calcium pantothenosulfonate, boldine, diacetylboldine or lily extracts, in particular lily bulb extracts;
  agents for combating free radicals or anti-inflammatory agents, such as an *Artemisia capillaris* extract, a *Sanguisorba officinalis* extract, resveratrol and its derivatives, turmeric or curcumin or tetrahydrocurcumin, polyphenols extracted from grape seeds, vitamin E and its derivatives, in particular its phosphate derivatives, ergothioneine or its derivatives, or idebenone;
  magnesium aspartateor adenosine, for improving the anti-wrinkle action;
  D-xylose, for improving the plumping effect for plumped skin;
  and any one of their mixtures.

The action of the combination of the three active principles described above can be supplemented by an anti-aging active agent which acts on the synthesis of lipids for a relipidizing effect which improves the barrier function or an anti-aging active agent which moderates the microinflammations involved in the aging process.

Advantageously, the composition additionally comprises at least one cosmetically acceptable excipient which can be chosen from segments, dyes, polymers, surfactants, rheology agents, fragrances, electrolytes, pH adjusters, preservatives and their mixtures.

The cosmetic composition can, for example, be a serum, a lotion, a cream (oil-water emulsion) or else a hydrogel, preferably a mask, or also be provided in the form of a stick or of a patch.

In a specific embodiment, the composition is provided in the form of an anti-aging serum comprising more than 85% by weight of water, preferably more than 95% by weight of water.

In another embodiment, the composition is provided in the form of an oil-and-water emulsion comprising up to 40% by weight, preferably up to 30% by weight, of a fatty phase, with respect to the total weight of the composition.

A second subject matter of the invention relates to a cosmetic care method comprising the topical application i) of the composition described above or ii) of the combination of an extract of the brown alga *Laminaria digitata*, of a *Saccharomyces* hydrolysate and an ascorbic acid or one of its esters to skin exhibiting signs of intrinsic and/or extrinsic aging, such as wrinkles, fine lines, a loss of elasticity, slackening or withering.

The composition or the combination of the three compounds is applied to the skin of an individual preferably with an age of more than 30 years, more than 35 years and more preferably more than 40 years.

According to one embodiment, the composition containing
  between 0.005 and 0.02%, preferably between 0.007 and 0.015%, and more preferably between 0.009 and 0.011% by weight of the extract of the brown alga *Laminaria digitata*, with respect to the weight of the composition,
  between 0.001 and 0.05%, preferably between 0.003 and 0.01%, and more preferably between 0.004 and 0.006% by weight of the *Saccharomyces* hydrolysate, with respect to the weight of the composition,
  between 0.05 and 0.5%, preferably between 0.1 and 0.3%, and more preferably between 0.15 and 0.25% by weight of ascorbic acid or one of its esters, with respect to the weight of the composition,
is applied to the skin in a proportion of 1 to 5 mg/cm$^2$, preferably of the order of 2 mg/cm$^2$.

Finally, a third subject matter of the invention relates to the use of the combination of an extract of the brown alga *Laminaria digitata*, of a *Saccharomyces* hydrolysate and of ascorbic acid or one of its esters for simultaneously i) increasing the synthesis of collagen I or of its precursor, procollagen I, and ii) having at least one other effect chosen from the expression of GAGs, the synthesis of elastin and the expression of integrins in the skin of an individual.

The invention also relates to the cosmetic composition comprising a cosmetically acceptable excipient and the combination of an extract of brown alga *Laminaria digitata*, of a *Saccharomyces* hydrolysate and ascorbic acid or one of its esters for its use in the treatment or prevention of aging of the skin, in particular of the dermis of the skin, preferably in an individual aged more than 30 years.

It makes it possible in particular to reduce the intensity of the wrinkles and fine lines and to restore the structure of the extracellular matrix constituting the dermis. It brings about an effect of tightening the surface of the skin by restoring the network of collagen fibers. This tightening effect is perceptible on the contours of the face.

The invention will be illustrated in more detail by the following implementation examples.

EXAMPLE 1

Tests on Fibroblasts

The influence of the extracts constituting the combination of the invention on the synthesis of procollagen I by normal human fibroblasts (NHF) is studied. Procollagen is a precursor form of collagen secreted in the extracellular medium where the ends are cut in order to result in the collagen subunit. The combining of these collagen molecules will subsequently create the collagen fibers.

Materials and Methods

1. Cell Model

Type: Normal human fibroblasts (NHF, donor aged 37 years), aged by passages in culture ($20^{th}$ passage).

Culturing conditions: 37° C., 5% $CO_2$.

Culture medium: (Invitrogen 21090-22) supplemented with L-glutamine 2 mM, penicillin 50 UI/ml-streptomycin 50 µg/ml, 10% FCS (Biowest S1810).

Test medium: 1% culture medium in fetal calf serum (FCS).

The active agents are dissolved in the culture medium at the concentration specified in the following table.

| Commercial name/Supplier | INCI name | Doses tested On cultured fibroblasts |
| --- | --- | --- |
| Raffermine ®/Silab | Hydrolyzed Soy Flour | 0.035% |
| Seanergilium ® BG/BASF | *Laminaria digitata* extract (and) Butylene Glycol | 0.02% |
| Biodynes ® TRF ® improved 25/ARCH | Water & *Saccharomyces* Lysate Extract | 0.005% |
| Vitamin C | Ascorbic acid | 0.002% |

2. Culturing and Treatments

The synthesis of type I procollagen by these cells was evaluated by the ELISA technique from the culture supernatants of aged fibroblasts.

The NHFs are cultured in a 96-well microplate at the rate of 7500 cells/well for 24 hours. At 80% confluence, the medium is replaced with the test medium containing the active agents to be tested or the references. The cells are incubated for 72 hours. The culture supernatants are subsequently recovered and stored at −20° C. while awaiting assaying. Assaying of the total proteins (BCA) is carried out on the cell layer.

The assaying of the procollagen I is carried out using an ELISA kit (Takara).

The amounts of procollagen I are expressed as ng/mg of protein.

Results

In each experiment, the series of control values and of treated values were compared using a Student test (unpaired series). The differences are significant for values of $p<0.05$.

1. Effects of the Active Agents Alone

The results obtained for each of the active agents tested alone are presented in the table below.

| no | Active agent | Procoll. I (ng/mg of prot) | Variation | Significance vs control |
| --- | --- | --- | --- | --- |
|  | Untreated control | 1439 ± 161 | — |  |
| 1 | Raffermine ® | 3755 ± 56 | +154% | S |
| 2 | Seanergillum ® | 2604 ± 203 | +81% | S |
| 3 | Biodynes ® | 2469 ± 214 | +72% | S |
| 4 | Vitamin C | 2431 ± 55 | +67% | S |

S = significant

These results are used below to compare the effect of combinations of two or three of these active agents, with respect to the expected theoretical effect calculated from the values obtained for each active agent individually.

2. Effects of the Combination of Two Active Agents, Including One Based on a *Saccharomyces* Extract The table below combines the results obtained for the different combinations of active agents with the yeast (*Saccharomyces*) extract:

| no | Active agent combined with Biodynes ® | Pro Coll. I (ng/mg of prot) | Variation | Significance vs control |
| --- | --- | --- | --- | --- |
|  | Untreated control | 1427 ± 154 | — |  |
| 5 | Raffermine ® + Biodynes ® | 3996 ± 227 | +180% | S |
| 6 | Seanergillum ® + Biodynes ® | 2321 ± 172 | +63% | S |
| 7 | Vitamin C + Biodynes ® | 2780 ± 390 | +95% | S |

When the result obtained for each of the above combinations is compared with the expected theoretical effect calculated from the values obtained in section 1, it is noted that the combination based on a yeast extract does not provide any measurable synergistic effect. The activity measured for a combination is always less than that calculated.

|  | Activity measured | Activity calculated |
| --- | --- | --- |
| Raffermine ® + Biodynes ® | +180% | +226% |
| Seanergillum ® + Biodynes ® | +63% | +153% |
| Vitamin C + Biodynes ® | +95% | +139% |

3. Effects of a Combination of Two Active Agents, Including One Based on Ascorbic Acid Results obtained for different combinations based on ascorbyl-2-glucoside are shown in the table below.

| Test | Pro Coll. I Mean (ng/mg of prot) | Variation | Significance vs control |
| --- | --- | --- | --- |
| Untreated control | 1033 ± 174 | — |  |
| 8 Raffermine ® + Vitamin C | 4957 ± 907 | +380% | S |
| 9 Seanergillum ® + Vitamin C | 4822 ± 740 | +367% | S |
| 10 Biodynes ® + Vitamin C | 2016 ± 83 | +95% | S |

For two of the three combinations, the ascorbyl-2-glucoside very significantly potentiates the synthesis of procollagen I. The results of the table below also confirm that the yeast extract does not appear to be a good candidate in a combination (in this instance with ascorbic acid) for simulating synthesis of procollagen I.

|  | Activity measured | Activity calculated |
|---|---|---|
| Raffermine ® + Vitamin C | +380% | +221% |
| Seanergillum ® + Vitamin C | +367% | +148% |
| Biodynes ® + Vitamin C | +95% | +139% |

4. Effects of a Combination of Three Active Agents, Including One Based on Ascorbic Acid and One Based on Yeast Extract The results obtained for these different combinations of three active agents are combined in the table below:

| no | Test | Mean (ng/mg of prot) | Variation | Significance vs control |
|---|---|---|---|---|
|  | Control | 258 ± 22 | — |  |
| 11 | Raffermine ® + Biodynes ® + Vitamin C | 996 ± 37 | +286% | S |
| 12 | Seanergillum ® + Biodynes ® + Vitamin C | 1567 ± 71 | +507% | S |

The activity measured for the combination of the three active agents is compared below with the theoretical activity calculated from the activity with each of the active agents taken separately.

Raffermine®+Biodynes®+Vitamin C

| no | Activity measured | Activity calculated |
|---|---|---|
| 11 | +286% |  |
| 1 + 3 + 4 |  | +293% |

For this combination, it is found that the activity measured is slightly lower than the expected activity calculated from the preceding tests. No synergy capable of reserving such a combination for the treatment of skin aging is observed.

Seanergillum®+Biodynes®+Vitamin C

| no | Activity measured | Activity calculated |
|---|---|---|
| 12 | +507% |  |
| 2 + 3 + 4 |  | +220% |

The combination exhibits a synergistic effect on the synthesis of procollagen I. This is because it is found that, in the case of the combination comprising the extract of the brown alga *Laminaria digitata*, a yeast extract and ascorbic acid, the activity measured is very markedly greater than that expected.

It is also observed, very surprisingly, that, in the case of the combination of the invention and contrary to the preceding combination, a negative effect related to the presence of the yeast extract is not measured and that, on the contrary, the positive effect measured with regard to the synthesis of procollagen I is much greater than that measured or calculated for all the combinations previously tested.

This combination is thus particularly advantageous in combating the appearance of signs of skin aging, in the form of cosmetic compositions.

EXAMPLE 2

Tests on Model of Old Skin Maintained Under Survival Conditions

The purpose of this study is to explore the anti-aging activity of cosmetic formulations on the epidermal and dermal structures of human skin explants ex vivo.

This activity is evaluated by visualization of the glycosaminoglycans (or GAGs), immunolabeling of the collagen I, immunolabeling of the elastin and immunolabeling of the integrin beta-1.

Explants with a diameter of 10 mm are prepared from abdominal plastic surgery on a woman aged 50 years. The explants were placed under survival conditions in BEM (BIO-EC's Explants Medium) medium at 37° C. in a humid atmosphere, enriched in 5% of $CO_2$.

Conditions of the Study:

Different cosmetic compositions of the invention and comparative compositions are tested. The cosmetic compositions of the invention comprise the combination of the invention consisting of an extract of the brown alga *Laminaria digitata*, of a yeast extract and of an ester of ascorbic acid.

Each cosmetic composition thus comprises:
0.01% by dry weight of Seanergilium® BG/BASF (*Laminaria digitata* extract),
0.005% by dry weight of Biodynes® TRF® improved 25/ARCH (*Saccharomyces* extract) and
0.2% by weight of ascorbyl-2-glucoside, an ester of ascorbic acid.

These cosmetic compositions have a content of glycols unchanging at 7% by weight and different from one another by a variable proportion of fatty phase.

The textures tested are as follows:
an oil-water (O/W) emulsion comprising 20% by weight of fatty phase, denoted $E_{20}$,
a placebo O/W emulsion, devoid of the combination of the invention, comprising 20% by weight of fatty phase, denoted Placebo Emulsion $P_{20}$,
an O/W emulsion comprising 10% by weight of fatty phase, denoted $E_{10}$,
a gelled serum comprising 1.5% by weight of fatty phase, denoted S.

For each cosmetic composition to be tested, five successive applications of a dose of 2 mg per $cm^2$ are carried out on a skin explant at D0, D2, D4, D6 and D8. Thus, at least three explants, for example 6, are prepared, on which the measurement of each marker is carried out at D9 or at D10. For each marker, the mean of all the explants prepared is produced.

The expression of the GAGs is evaluated by trichrome staining of the sections of explants produced in paraffin. The staining is subsequently evaluated with a microscope by image analysis.

The elastin, collagen I and integrin beta-1 are quantified by immunolabeling and microscopic analysis.

For each marker tested, the results obtained on the skin explants under survival conditions are expressed as percentages of variation with respect to the untreated control, solely for the specifically significant results.

The non-significant variations are denoted NS.

The variations in activity, as percent symbol with respect to an untreated control, for an emulsion comprising 20% by weight of polyphase, comprising or not comprising the combination of the invention, are shown in the table below:

| Formulations/UT Control D10 | GAGs | Collagen I | Integrin beta-1 |
|---|---|---|---|
| Placebo Emulsion $P_{20}$ | NS | NS | NS |
| Emulsion $E_{20}$ | +51% | +43% | +50% |

It is shown that the cosmetic compositions of the invention exhibit a significant activity with regard to a large number of markers; that is not the case for the placebo emulsion (Placebo Emulsion $P_{20}$).

The test is also carried out using an emulsion comprising a fatty phase in a lower proportion.

The variations in activity, as percentage with respect to untreated control, for each of the markers tested, are expressed in the table below:

| Formulations/UT Control D9 | GAGs | Collagen I | Elastin |
|---|---|---|---|
| Gelled serum S | +60% | +126% | +33% |
| Emulsion $E_{10}$ | +44% | +140% | NS |

The combination thus shows all its advantage as anti-aging active agents in varied products intended for the care of elderly skin or skin exhibiting signs of skin aging.

The results obtained both for the combination itself or for cosmetic compositions comprising the combination of the invention demonstrate the effectiveness of the combination of the invention in cosmetic compositions which exhibit different cosmetic textures for caring for or making up the skin.

The combination of the invention significantly stimulates different markers strongly implicated in skin aging, such as GAGs, elastin or integrin beta-1.

Among the compositions for the skin, the gelled serum, which exhibits the lowest proportion of fatty phase, shows a high effectiveness with regard to the greatest number of markers tested.

The combination of the invention, for which a synergistic effect with regard to the synthesis of procollagen I has been shown, also produces an advantageous effect with regard to other markers of aging, in particular collagen I.

The combination thus exhibits an advantage of the first order for use in anti-aging compositions, or care or make-up methods targeted at combating the appearance of signs of skin aging or at slowing down the development thereof.

The invention claimed is:

1. A cosmetic composition comprising at least one cosmetically acceptable excipient, and a mixture consisting of:
   between 0.005 and 0.02% by weight of an extract of the brown alga *Laminaria digitata*, with respect to the weight of the composition,
   between 0.003 and 0.01% by weight of a *Saccharomyces* hydrolysate, with respect to the weight of the composition, and
   between 0.01 and 0.3% by weight of ascorbic acid or one of its esters, with respect to the weight of the composition.

2. The cosmetic composition of claim 1, wherein the ratio by weight of the extract of the brown alga *Laminaria digitata* to the *Saccharomyces* hydrolysate is between 1/1 and 5/1.

3. The cosmetic composition of claim 1, wherein the ratio by weight of the ascorbic acid or one of its esters to the *Saccharomyces* hydrolysate is between 10/1 and 100/1.

4. The cosmetic composition of claim 1, wherein the composition contains:
   between 0.007 and 0.015% by weight of the extract of the brown alga *Laminaria digitata*, with respect to the weight of the composition,
   between 0.003 and 0.01% by weight of the *Saccharomyces* hydrolysate, with respect to the weight of the composition,
   between 0.1 and 0.3% by weight of ascorbic acid or one of its esters, with respect to the weight of the composition,
   wherein the composition is suitable for being applied on a person's skin in a proportion of 1 to 5 mg/cm$^2$.

5. The cosmetic composition of claim 1, wherein the extract of the brown alga *Laminaria digitata* is obtained by a process comprising a step of grinding the fresh alga, said step being followed by the steps of maturation in water, separation, settling and filtration.

6. The cosmetic composition of claim 1, wherein the *Saccharomyces* hydrolysate is obtained by a process comprising the steps of:
   irradiation of a suspension of the living yeast with UV light and/or heat,
   hydrolysis by a proteolytic enzyme, and
   collection of the filtrate.

7. The cosmetic composition of claim 1, wherein the composition is provided in the form of an anti-aging serum comprising more than 85% by weight of water or of an oil-in-water emulsion comprising up to 40% by weight of a fatty phase, the percentages being expressed with respect to the total weight of the composition.

8. The cosmetic composition of claim 1, wherein the composition is provided in the form of a gelled serum comprising 1.5% by weight of a fatty phase.

9. The cosmetic composition of claim 1, wherein the ratio by weight of the ascorbic acid or one of its esters to the *Saccharomyces* hydrolysate is between 30/1 and 40/1.

10. The cosmetic composition of claim 1, wherein the ascorbic ester is ascorbyl-2 glucoside.

* * * * *